US00PP08597P

United States Patent [19]

Viscarra

[11] Patent Number: Plant 8,597

[45] Date of Patent: Feb. 15, 1994

[54] "SPECIAL RED JULY" PEACH TREE

[76] Inventor: Federico E. Viscarra, 19728 E. Parlier Ave., Reedley, Calif. 93654

[21] Appl. No.: 907,648

[22] Filed: Jul. 2, 1992

[51] Int. Cl.[5] ..... A01H 5/00

[52] U.S. Cl. ..... Plt./43.2

[58] Field of Search ..... Plt. 42.1, 43.2, 43.3, Plt. 41.1

*Primary Examiner*—James R. Feyrer
*Assistant Examiner*—E. F. McElwain
*Attorney, Agent, or Firm*—Worrel & Worrel

[57] ABSTRACT

A new and distinct variety of peach tree which is somewhat remotely similar to the "Elegant Lady" peach tree (U.S. Plant Pat. No. 4,399) and the "O'Henry" peach tree (U.S. Pat. No. 2,964), but from which it is distinguished by producing fruit which is mature for harvesting and shipment approximately July 22 to August 5 in the central San Joaquin Valley of California, the fruit being freestone having an oval shape and which further exhibits a highly colored and very firm light yellow flesh.

1 Drawing Sheet

BACKGROUND OF THE NEW VARIETY

The present invention relates to a new and distinct variety of peach tree, which will hereinafter be denominated varietally as the "Special Red July" peach tree, and, more particularly, to such a peach tree which produces freestone fruit which is mature for commercial harvesting and shipment approximately July 22 to August 5 in the San Joaquin Valley of central California, and which is further distinguished by the fruit being large, highly colored, productive and very firm and which hangs well on the tree so that it can be harvested over an extended two week period.

The discovery and development of new commercial varieties of fruit is a science dependent upon many years of observation of the myriad of individual characteristics of a multitude of varieties, a full knowledge of the critical characteristics of the best existing commercial varieties, a knowledge of the markets for the fruit thereof and a substantial amount of good fortune. Since the value of new varieties of fruit bearing trees is largely dependent upon the commercial acceptance of the fruit thereof, those attributes which enhance the attractiveness of the fruit to consumers generally receive the greatest scrutiny. Thus, size, coloration, flavor and the like are very important. Perhaps less obviously, but of equal importance, are such attributes as ripening time, productivity, holding quality, resistance to damage and resistance to disease and to pests. These qualities are of significance in ensuring that the fruit can be made available to the consumer at the best time, in the best possible condition and in commercially practical volume.

The fruit of the "Special Red July" peach tree of the subject invention possesses an unusually attractive combination of many of these commercial attributes. As will hereinafter be described in greater detail, the peach tree of the subject invention produces large, highly colored fruit having unusually firm flesh with superior holding qualities and ripening during a time period complementing existing commercial varieties.

ORIGIN AND ASEXUAL REPRODUCTION OF THE NEW VARIETY

The "Special Red July" peach tree was discovered by the applicant as a spontaneous mutation of the "Spring Red" nectarine tree (U.S. Plant Pat. No. 3,619) on the applicant's property in Orosi in the central valley of California. The discovery took place on May 10, 1988 when the applicant noted the distinctive characteristics hereinafter to be described. The applicant asexually reproduced the new variety in January, 1989 by grafting wood taken from the spontaneous mutation, appearing as a small hangar-like limb occurring at a height of approximately seven feet from the ground on the parent tree, on to a "Spring Red" nectarine tree on the same property. The applicant has continued to observe the asexually reproduced peach tree of the new variety and has confirmed that it has the same distinctive characteristics as the original spontaneous mutation.

SUMMARY OF THE NEW VARIETY

The peach tree is characterized as to novelty by producing a very firm fleshed freestone fruit which has a deep garnet red coloration with substantial light colored speckles present. Further, the fruit produced by the "Special Red July" peach tree is ripe for commercial harvesting and shipment approximately July 22 through August 5 in the San Joaquin Valley of central California. The variety is most closely similar to the "Elegant Lady" peach tree (U.S. Plant Pat. No. 4,399) and the "O'Henry" peach tree (U.S. Plant Pat. No. 2,964), but is distinguishable therefrom and characterized principally as to novelty by producing fruit which are ripe for harvesting and shipment approximately two weeks after the "Elegant Lady" peach tree and approximately one week before the "O'Henry" peach tree. The instant variety produces a fruit with a blush color which is generally darker and slightly more dull than that of the "Elegant Lady" peach tree and has more speckling and russets than is found on either the "O'Henry" or the "Elegant Lady" peach trees.

BRIEF DESCRIPTION OF THE DRAWING

The accompanying drawing is a color photograph showing a branch with typical foliage of the new variety bearing two whole fruit thereof, a second fruit of the new variety shown in side elevation, a third sectioned and with the stone removed to expose the pit well, a fourth sectioned with the stone left in place and two stones, all of the new variety.

DETAILED DESCRIPTION

Referring more specifically to the pomological details of this new and distinct variety of peach tree, the following has been observed under the ecological conditions prevailing at the orchard of origin which is located in Orosi, Calif. All major color code designations are by reference to the *Dictionary of Color*, by Maerz and Paul, First Edition, 1950. Common color names are also occasionally employed.

TREE

Generally:

*Vigor.*—Vigorous and hardy under normal climatic conditions in the central San Joaquin Valley of California.

*Figure.*—Upright to upright-spreading form. However, the eventual tree form can be substantially modified by pruning.

*Productivity.*—Productive.

*Regularity of bearing.*—Regular.

Trunk:

*Size.*—Medium in thickness 17.5 cm (6.889 inches) in diameter.

*Surface texture.*—Normal.

*Color.*—Dark grey-brown (Rembrandt brown 8-H-9).

*Lenticels — numbers.*—Average.

*Lenticels — length.*—6 mm (0.2362 inches) to 15 mm (0.5905 inches).

*Lenticels — height.*—3 mm (0.1181 inches) to 7 mm (0.2755 inches).

Branches:

*Size.*—Average in thickness.

*Surface texture.*—Normal.

*Color — one year or older wood.*—Light grey-brown (Liberia brown 8-J-7).

*Color — immature branches.*—Pale green (Sea green 19-K-6) and tinged with a red shading where the shoot are exposed to direct sunlight.

LEAVES

Size:

*Generally.*—Average.

*Average length.*—18.4 cm (7.244 inches) including petiole. Leaf measurements are from leaves growing at the midpoint of upright, vigorous, actively growing current season's shoots.

*Average width.*—4.2 cm (1.653 inches).

Leaf thickness: Average for species.

Form: Linear lanceolate with an acuminate tip. Apex is often twisted.

Color:

*Upwardly disposed surface.*—Deep green (23-L-8).

*Downwardly disposed surface.*—Lighter green (Cress green 22-K-6).

Marginal form:

*Generally.*—Crenate, with low, regular crenations.

Leaf margin: Slightly undulate.

Grandular characteristics:

*Glands.*—Medium to large in size and usually reniform in form. Three to five strongly reniform glands in alternate positions are present along the base of the leaf margin. In addition, one or two more glands can occasionally occur on stalks at the very base of the leaf margin or on the petiole very close to the basal margin. These glands are less strongly reniform and can on occasion be nearly globose.

Leaf gland color: Light shiny green (Calliste green 19-L-6) when the leaf is young, darkening and deteriorating with age.

Petiole:

*Size.*—Medium.

*Length.*—9 mm (0.3543 inches) to 11 mm (0.4330 inches).

*Thickness.*—2.0 mm (0.0787 inches).

*Color.*—Light green (Sea green 19-K-6) with color slightly darker on the upper petiole along the petiole groove (Lettuce green 20-L-5).

Stipules: Medium to moderately long. Stipules are early deciduous.

*Length.*—7 mm (0.2755 inches) to 10 mm (0.3937 inches) on vigorous leaves.

*Form.*—Lanceolate with coarse, serrate margins.

*Color.*—Light green (18-L-7), darkening with age.

FLOWERS

Flower buds:

*Size.*—Medium and conic in form.

Flower bud scales:

*Color.*—Dark brown (Cordova brown 7-J-11). Bud scales highly pubescent with a grayish colored pubescence.

Flowers:

*Generally.*—Flowers never completely expand, even at full maturity, but remain partially closed and cupped inwards.

Date of Full Bloom: March 10 in 1991. Average in relation to the bloom of other common commercial peach varieties.

Bloom quantity: Abundant. Most often two flower buds are present per node.

Size:

*Generally.*—Medium. Non-showy in form. Size of bloom for this cultivar is in the upper size range for this form. Average diameter of flower when fully expanded is 24 mm (0.9448 inches).

Petals: Petal claw is short, moderately broad and truncate. The petals are strongly cupped and rolled inwards. Petal margins are moderately undulate. Petal apex is rounded.

*Color.*—Bright pink (1E-1), darker basally and on the claw (1-J-3).

*Number.*—Five.

*Form.*—Generally ovate to oval.

*Length.*—Average 15.5 mm (0.6102 inches).

*Width.*—Average 9 mm (0.3543 inches).

Pedicel:

*Surface.*—Glabrous.

*Length.*—Medium, 2.0 mm (0.0787 inches).

*Thickness.*—1.5 mm (0.0590 inches).

*Color.*—Green (21-L-4).

Nectaries:

*Color.*—Dull orange (11-H-11).

Anthers:

*Size.*—Average.

*Color.*—Tan (11-G-3) ventrally and red (4-K-10) dorsally.

Pollen: Abundant.

*Color.*—Yellow (10-L-3).

Stamens:

*Length.*—Medium, 18 mm (0.7086 inches). Nearly equal in length to pistil when fully expanded.

*Color.*—Light pink (1-C-1) when young, darkening to a medium violet (4-J-3) with age.

Pistil:

*Length.*—Averages 17 mm (0.6692 inches) to 18 mm (0.7086 inches) including ovary.

*Surface.*—Highly pubescent.

*Color.*—Light green (18-H-2).

FRUIT

Maturity when described: Ripe for commercial harvesting and shipment approximately July 22 through August 5 in 1991 near Orosi, Calif.

Size:

*Generally.*—Large and uniform.

*Average diameter in the axial plane.*—82 mm (3.228 inches).

*Average diameter in the cheek plane.*—78 mm (3.070 inches).

*Average diameter tranverse in the suture plane.*—76 mm (2.992 inches).

Form:

*Uniformity.*—Variable, from oval to slightly ovate in lateral aspect. Nearly globose in apical aspect.

*Symmetry.*—Most frequently asymmetrical with one half of the fruit larger than the other.

Suture:

*Generally.*—A visible line present from base to apex. The suture is often cleft over the basal shoulder. The suture deepens over the apical shoulder, becoming distinctly depressed next to the apex.

*Depth.*—4 mm (0.1574 inches) to 8 mm (0.3149 inches).

*Color.*—Variable, most often taking on the color of the underlying blush or ground color, but occasionally displaying a light red (Korea red 5-J-11) striping along a portion of the suture itself.

Ventral surface:

*Generally.*—Variable, from rounded, especially at mid-suture to substantially lipped at the apical and basal shoulders of the suture.

Stem cavity:

*Generally.*—Medium to below average in size.

*Width.*—25 mm (0.9842 inches).

*Depth.*—Moderately deep, averaging 14 mm (0.551 inches).

*Length.*—26 mm (1.023 inches).

*Shape.*—Oval to nearly globose.

Stem:

*Generally.*—Medium in length and moderately thick.

*Thickness.*—Averaging 3.5 mm (0.1377 inches).

*Length.*—10 mm (0.3937 inches) to 12 mm (0.4724 inches).

*Color.*—Light green (20-K-3).

Base: Variable, from rounded to slightly truncate. Base angle most often slightly oblique to the fruit axis.

Apex:

*Shape.*—Variable, from rounded to slightly pointed.

Pistil point: Most often strongly oblique.

Skin: Low in acidity and tenacious to flesh at commercial maturity. Skin color is variable throughout the fruit surface.

*Thickness.*—Medium with very short, fine pubescence.

*Texture.*—Very firm and fine textured.

*Tendency to crack.*—None observed.

*Blush color.*—Orange-red (3-H-11), darkening to a deeper garnet-red (7-J-6). Substantial dappling is present within these shades of red. Blush color amount ranges from 70 to 95 percent of the fruit surface. Substantial numbers of light colored dots, speckles and light russet are present both laterally and over the apex and apical shoulders.

*Ground color.*—Amber-yellow (10-K-4).

*Flesh color.*—Basic color is light amber-yellow (10-J-2 Mimosa yellow), slightly darker just beneath the skin.

*Surface of pit cavity.*—A considerable amount of red coloration is present within, and radiating out from the pit cavity (Flash red 3-K-11).

*Flavor.*—Well balanced with moderate acidity.

*Aroma.*—Moderate.

*Texture.*—Very firm and fine textured.

*Ripening.*—Ripens evenly.

*Eating quality.*—Good.

Stone:

*Attachment.*—Freestone.

*Fibers.*—Some slight fiber attachment along the ventral suture.

*Fibers — length.*—A few medium length fibers are attached to the stone along the ventral suture.

*Size.*—Medium to small.

*Size — length.*—Averages 37 mm (1.456 inches).

*Size — width.*—Averages 26 mm (1.023 inches).

*Size — thickness.*—Averages 20 mm (0.7874 inches.

*Form — generally.*—Somewhat variable and irregular. Roughly oval to slightly obovate.

*Apex — shape.*—Apical shoulders are generally rounded with a sharp dentate apex.

*Color — dry.*—Medium brown (Rustic brown 7-H-11). Often, areas of the stone surface, especially in the basal shoulder area, are stained with red coloration from the red pit cavity.

*Base — shape.*—Broad and truncate in form. Base angle is most frequently oblique to stone axis.

*Sides — generally.*—Most frequently unequal.

*Hilum.*—Large in size and distinctly oval in form. The hilum is surrounded by a relatively thick and grooved collar.

*Stone surface.*—Very rough, ridged and pitted. Large pits are present especially laterally at about mid-stone. The most substantial ridges and grooves are also present laterally over the apical shoulders. Basally, less pronounced grooves and ridges are present, converging basally.

*Ventral edge.*—Relatively broad, averaging 6 mm (0.2362 inches) at mid-suture. The ventral edge is variable, at times several medium size wings are present, coalseced basally and converging apically. These wings are most prominent at mid-suture. At other times a large prominent wing is present, from 5 mm (0.1968 inches) to 6 mm (0.2362 inches) in height, and occurring over the basal shoulder.

*Dorsal edge.*—A large groove is present on this edge, extending from the base to slightly above mid-stone. This groove is subtended by two ridges, usually deeply cut by cross grooves. The apical shoulder of the dorsal edge is substantially eroded and nearly concave, with a smaller, tighter groove.

*Tendency to split.*—None observed.

Use: This new peach is a mid to late season fresh market variety, suitable for both local market and long distance shipping.

Although the new variety of peach tree possesses the described characteristics noted above as a result of the growing conditions prevailing near Orosi, Calif. in the central part of the San Joaquin Valley of California, it is to be understood that variations of the usual magnitude and characteristics incident to changes in growing conditions, irrigation, fertilization, pruning and pest control are to be expected.

Having thus described and illustrated my new variety of peach tree, what I claim as new and desire to be secured by Plant Letters Patent is:

1. A new and distinct variety of peach tree substantially as illustrated and described which was derived as a spontaneous mutation of the "Spring Red" nectarine tree (U.S. Plant Pat. No. 3,619) and which is somewhat remotely similar to the "Elegant Lady" peach tree (U.S. Plant Pat. No. 4,399) and the "O'Henry" peach tree (U.S. Plant Pat. No. 2,964), but from which it is distinguished by producing a freestone fruit which is mature for harvesting and shipment approximately July 22 to August 5 in the San Joaquin Valley of central California, the fruit having from an orange-red to a deeper garnet-red coloration having substantial light colored speckles present and a flesh which is a light amber-yellow and of a very firm texture at commercial maturity.

* * * * *

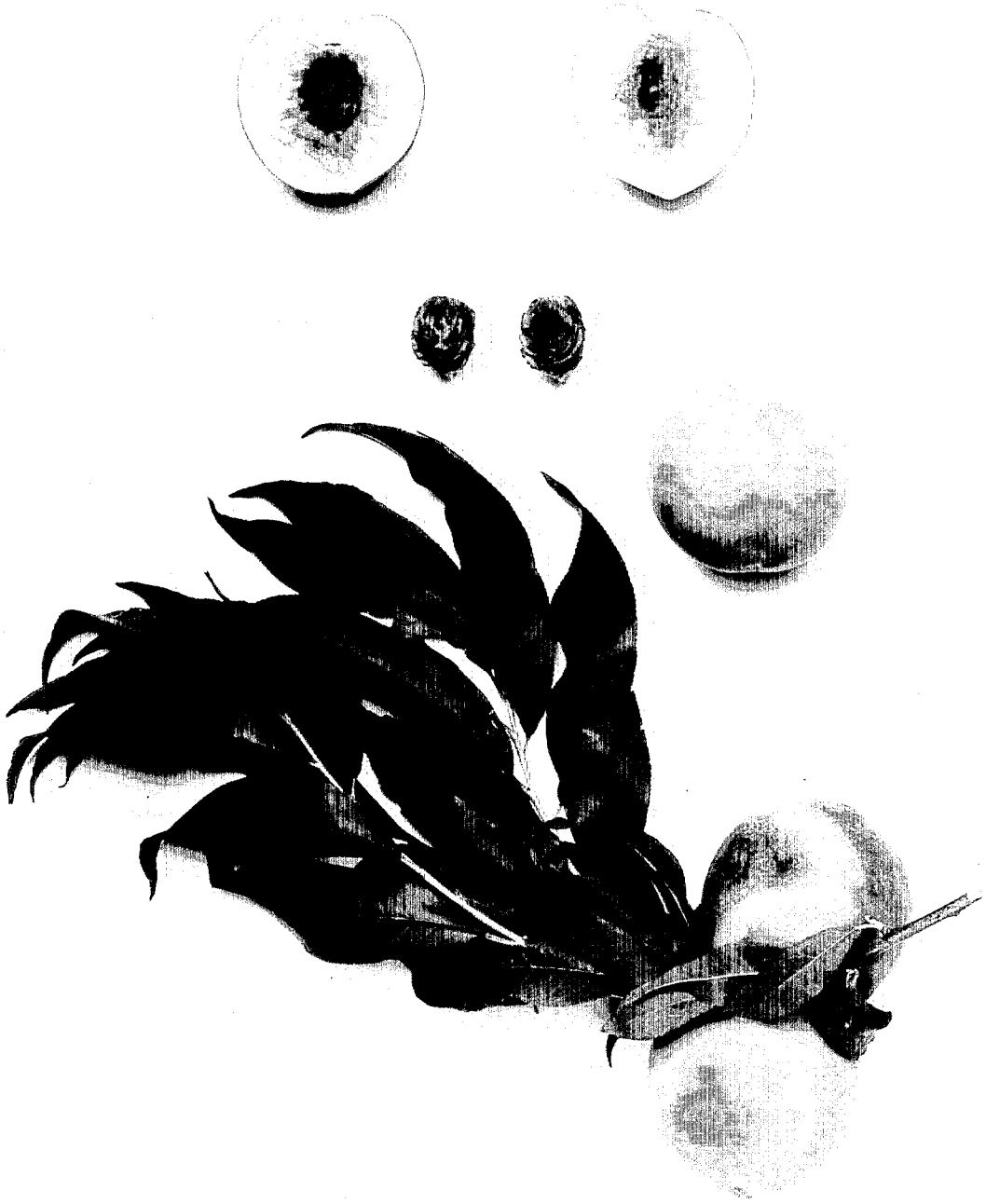

UNITED STATES PATENT AND TRADEMARK OFFICE

CERTIFICATE OF CORRECTION

PATENT NO. : Plant 8,597

DATED : February 15, 1994

INVENTOR(S) : Federico E. Viscarra

It is certified that error appears in the above-identified patent and that said Letters Patent is hereby corrected as shown below:

Column 4, line 47, delete "(1E-1)" and substitute ---(1-E-1)---.

Column 6, line 30, delete "(0.7874 inches." and substitute ---(0.7874 inches).---

Column 6, line 55, delete "coalseced" and substitute ---coalesced---.

Signed and Sealed this

Eleventh Day of October, 1994

Bruce Lehman

*Attest:*

BRUCE LEHMAN

*Attesting Officer*

*Commissioner of Patents and Trademarks*